United States Patent [19]

Sinofsky et al.

[11] Patent Number: 5,100,429
[45] Date of Patent: Mar. 31, 1992

[54] ENDOVASCULAR STENT AND DELIVERY SYSTEM

[75] Inventors: Edward L. Sinofsky, Peabody; Gary L. Boseck, Boxford; Edward I. McNamara, Chelmsford, all of Mass.

[73] Assignee: C. R. Bard, Inc., Murray Hill, N.J.

[21] Appl. No.: 424,660

[22] Filed: Oct. 20, 1989

Related U.S. Application Data

[63] Continuation-in-part of Ser. No. 345,110, Apr. 28, 1989, abandoned.

[51] Int. Cl.$^5$ .................................. A61M 29/02
[52] U.S. Cl. ..................... 606/195; 604/96; 128/DIG. 8; 606/7; 623/1
[58] Field of Search ................... 604/96, 104; 128/DIG. 8; 606/191, 194, 195, 7, 8, 13–15; 623/1, 12

[56] References Cited

U.S. PATENT DOCUMENTS

| | | | |
|---|---|---|---|
| 3,173,418 | 3/1965 | Baran | 128/351 |
| 3,563,925 | 2/1971 | Kliment et al. | 260/8 |
| 3,625,745 | 12/1971 | Wright | 117/93.31 |
| 3,808,113 | 4/1974 | Okamura et al. | 204/159.12 |
| 3,949,073 | 4/1976 | Daniels et al. | 424/117 |
| 4,060,081 | 11/1977 | Yannas et al. | 128/156 |
| 4,319,363 | 3/1982 | Ketharanathan | 3/1.4 |
| 4,378,017 | 3/1983 | Kosugi et al. | 424/35 |
| 4,390,519 | 6/1983 | Sawyer | 424/28 |
| 4,403,612 | 9/1983 | Fogarty . | |
| 4,417,576 | 11/1983 | Baran | 128/207.15 |
| 4,423,725 | 1/1984 | Baran et al. . | |
| 4,445,892 | 5/1984 | Hussein et al. | 604/101 |
| 4,478,658 | 10/1984 | Wittwer | 156/69 |
| 4,485,096 | 11/1984 | Bell | 424/95 |
| 4,503,569 | 3/1985 | Dotter | 3/1.4 |
| 4,553,545 | 11/1985 | Maass et al. . | |
| 4,553,974 | 11/1985 | Dewanjee | 8/94.11 |
| 4,577,631 | 3/1986 | Kreamer . | |
| 4,578,067 | 3/1986 | Cran, Jr. | 604/380 |
| 4,589,882 | 5/1986 | Urry | 623/11 |
| 4,597,762 | 7/1986 | Walter et al. | 623/1 |
| 4,605,406 | 8/1986 | Cahalan et al. | 623/1 |
| 4,641,653 | 2/1987 | Rockey | 604/96 |
| 4,642,118 | 2/1987 | Kuroyanagi et al. | 623/15 |
| 4,695,281 | 9/1987 | Miyata et al. | 623/11 |
| 4,704,131 | 11/1987 | Noishiki et al. | 623/66 |
| 4,708,718 | 11/1987 | Daniels | 604/53 |
| 4,732,152 | 3/1988 | Wallsten et al. . | |
| 4,733,665 | 3/1988 | Palmaz . | |
| 4,740,207 | 4/1988 | Kreamer | 623/1 |
| 4,763,653 | 8/1988 | Rockey | 604/101 |
| 4,773,899 | 9/1988 | Spears | 604/20 |
| 4,799,479 | 1/1989 | Spears | 606/7 |
| 4,877,030 | 10/1989 | Beck et al. | 606/195 |
| 4,878,492 | 11/1989 | Sinofsky et al. | 606/7 |
| 4,923,464 | 5/1990 | Dipisa, Jr. et al. | 606/195 |

FOREIGN PATENT DOCUMENTS 8912478 12/1989 PCT Int'l Appl. ............... 604/104

OTHER PUBLICATIONS

*Science*, vol. 232, Jun. 13, 1986, pp. 1421–1422.

*Primary Examiner*—Stephen C. Pellegrino
*Assistant Examiner*—Ralph A. Lewis
*Attorney, Agent, or Firm*—Wolf, Greenfield & Sacks

[57] ABSTRACT

An uncured or partially cured, collagen-based material is delivered to a selected site in a blood vessel and is crosslinked in the blood vessel by laser energy or other suitable energy to form an endovascular stent. The collagen-based material can be delivered to the blood vessel as a coating on an inflatable balloon mounted on the distal end of a catheter. The collagen-based material can also be delivered to the blood vessel in liquid form and forced through a porous balloon to form a tubular configuration. The collagen-based material is preferably crosslinked by laser radiation carried through an optical fiber to a diffusing tip located within the balloon. In another embodiment, an endovascular stent is formed by rolling a flexible sheet of biologically-compatible material onto an outside surface of an inflatable balloon. A crosslinkable collagen-based adhesive is used to adhere overlapping portions of the sheet together in the blood vessel and can be used to attach the stent to an inside surface of the blood vessel. The collagen-based adhesive is crosslinked in the blood vessel by application of laser energy or other suitable energy. A photodegradable adhesive can be used on an inside surface of the stent to releasably attach the stent to the inflatable balloon.

44 Claims, 5 Drawing Sheets

ENDOVASCULAR STENT AND DELIVERY SYSTEM

CROSS REFERENCE TO RELATED APPLICATION

This application is a continuation-in-part of application Ser. No. 345,110 filed Apr. 28, 1989, now abandoned.

FIELD OF THE INVENTION

This invention relates to an endovascular stent for transluminal delivery to a blood vessel and, more particularly, to an endovascular stent comprising a sheet of biologically-compatible material that is rolled onto an inflatable balloon located at the distal end of a catheter for delivery to a selected site in the blood vessel.

BACKGROUND OF THE INVENTION

Balloon angioplasty is utilized to treat coronary arteries narrowed by plaque deposits. A catheter having an inflatable balloon secured to its distal end is advanced through the artery to the narrowed region. The balloon is inflated, causing the narrowed, or stenosed, region of the artery to be expanded The balloon is then deflated and withdrawn.

A serious problem associated with balloon angioplasty has been the occurrence in up to 30% of the cases of so-called restenosis, either immediately after the procedure or within about six months. Immediate restenosis, also known as abrupt reclosure, results from flaps or segments of plaque and plaque-ridden tissue which are formed during balloon angioplasty and which can block the artery. Such blockage of the artery requires emergency surgery and sometimes results in death. Furthermore, a surgical team is required to stand by during the balloon angioplasty procedure. Restenosis at a later time results from causes that are not totally known. Thrombus formation is believed to play an important part. Often, repeat balloon angioplasty or surgery is required, and another episode of restenosis may occur.

One approach to dealing with the problem of restenosis is to maintain a passage through the artery with an endovascular stent. The stent is a generally tubular device which is placed inside the blood vessel after balloon angioplasty or some other type of angioplasty has been completed. The stent has sufficient strength and resiliency to resist restenosis and to maintain a passage through the vessel. A catheter is typically used to deliver the stent to the stenosed site. U.S. Pat. No. 4,733,665, issued Mar. 29, 1988 to Palmaz, discloses a vascular stent comprising an expandable wire mesh tube. The stent is positioned over an inflatable balloon secured to a catheter and is advanced to the stenosed region. The balloon is inflated, thereby expanding the stent into contact with the vessel wall. The elastic limit of the wire mesh is exceeded when the balloon is expanded, so that the stent retains its expanded configuration. U.S. Pat. No. 4,503,569, issued Mar. 12, 1985 to Dotter, discloses a shape memory alloy stent that is advanced to a stenosed region on a catheter. The stent has the form of a coil spring. After positioning, the stent is heated with a hot fluid causing the shape memory alloy to expand into contact with the blood vessel. U.S. Pat. No. 4,740,207, issued Apr. 26, 1988 to Kreamer, discloses a plastic graft for repair of the vascular system. A catheter is suggested for placement of the graft in a coronary artery. Stents for placement in blood vessels are also disclosed in U.S. Pat. No. 4,553,545, issued Nov. 19, 1985 to Maass et al and U.S. Pat. No. 4,732,152, issued Mar. 22, 1988 to Wallsten et al. U.S. Pat. No. 4,577,631 issued Mar. 25, 1986 to Kreamer, discloses a Dacron blood vessel graft that is coated with an adhesive. The Kreamer patent states that the adhesive may be activated by ultraviolet or ultrasonic energy after placement in the aorta.

All known prior art vascular stents have been fabricated of metal or plastic and remain in the blood vessel indefinitely. The long term effects of such devices are not well known. Furthermore, such devices have a fixed range of expansion within the blood vessel. In some cases, the stent may be too small in diameter, even after expansion, to be affixed to the vessel wall, and in other cases the stent may expand to such a diameter that the vessel is damaged or ruptured. In either case, improperly sized or positioned prior art stents require surgery for removal.

It has been proposed in the prior art to use collagens and collagen-based compositions in skin grafts, bandages and vascular prostheses. An advantage of using collagen in such devices is that collagen occurs naturally in the human body, and the graft or prosthesis is eventually absorbed into the tissue to which it is attached. U.S. Pat. No. 4,319,363, issued Mar. 16, 1982 to Ketharanathan, discloses a vascular prosthesis for use as a surgical graft. The prosthesis comprises a tubular wall of Type I collagenous tissue. U.S. Pat. No. 4,390,519, issued June 28, 1983 to Sawyer, discloses a bandage wherein a collagen or collagen like substance is incorporated into the pad or sponge of the bandage. U.S. Pat. No. 4,642,118, issued Feb. 10, 1987 to Kuroyanagi et al, discloses a man-made skin including a collagen sponge layer and a poly alpha-amino acid membrane. U.S. Pat. No. 3,808,113, issued Apr. 30, 1974 to Okamura et al discloses a method for manufacturing medical articles comprising a polymer coated with collagen. In one step of the process, the collagen is irradiated with radioactive rays, an electron beam or ultraviolet radiation to fix the collagen layer.

U.S. Pat. No. 4,417,576, issued Nov. 29, 1983 to Baran, discloses a double wall surgical cuff for introduction into a body passage. The outer cuff is porous, and a sponge material is positioned between the inner and outer cuffs. A surgical fluid such as an anesthetic is absorbed by the sponge material. When the inner cuff is inflated, the fluid is driven through the porous outer cuff to the walls of the body passage.

It is a general object of the present invention to provide improved endovascular stents.

It is another object of the present invention to provide an endovascular stent in the form of a sheet of biologically-compatible material that is rolled into a tubular configuration.

It is a further object of the present invention to provide an endovascular stent in the form of a sheet of biologically-compatible material that is rolled onto the outer surface of an inflatable balloon for delivery to a blood vessel.

It is yet another object of the present invention to provide an endovascular stent having a crosslinkable adhesive material applied to an outer surface thereof for attaching the stent to a selected site in a blood vessel.

It is another object of the present invention to provide an endovascular stent in the form of a sheet of biologically-compatible material that is rolled into a tubular configuration, overlapping portions of the sheet being adhered together in a blood vessel with a crosslinkable adhesive material.

It is still another object of the present invention to provide an endovascular stent having a photodegradable adhesive on an inner surface thereof for releaseable attachment to an inflatable balloon.

It is yet another object of the present invention to provide an endovascular stent which is delivered to a selected site in a blood vessel and which is released from the inflatable balloon and attached to the blood vessel by the application of energy through the wall of the balloon.

SUMMARY OF THE INVENTION

According to the present invention, these and other objects and advantages are achieved in a method for treating a selected region of a blood vessel. The method comprises the steps of applying a crosslinkable adhesive material to one side of a flexible sheet of biologically-compatible material, rolling the sheet of biologically-compatible material so that portions of the sheet overlap to form a tubular body, the tubular body having the crosslinkable adhesive material between overlapping portions of the sheet, delivering the tubular body to the selected region of the blood vessel, and applying energy to the tubular body at the selected region of the blood vessel so as to crosslink the adhesive material and cause overlapping portions of the sheet to adhere together to thereby form a stent in the blood vessel.

Preferably, the crosslinkable adhesive material is a collagen-based material. The sheet can have a continuous surface or can be patterned with openings of various sizes and shapes. The sheet of biologically-compatible material is preferably rolled onto an outer surface of an inflatable balloon located at or near the distal end of a catheter, and the catheter is advanced through the blood vessel to position the balloon at the selected region. The balloon is inflated to thereby increase the diameter of the tubular body at the selected region of the blood vessel and urge the tubular body into contact with the inside surface of the blood vessel. Energy is preferably applied to the tubular body by applying diffused laser energy from within the balloon. The crosslinkable adhesive material can be applied to an outside surface of the tubular body such that the tubular body is attached to the blood vessel by the application of energy.

According to another aspect of the invention, a photodegradable adhesive is applied to the other side of the sheet of biologically compatible material prior to rolling the sheet onto the inflatable balloon so that the tubular body is adhered to the inflatable balloon by the photodegradable adhesive. Energy in a first wavelength range selected to degrade the photodegradable adhesive and release the tubular body from the inflatable balloon is applied to the tubular body from within the balloon.

According to a further feature of the invention, the photodegradable adhesive includes a fluorescent material that is stimulated by energy in the first wavelength range to emit energy in a second wavelength range required for crosslinking of the crosslinkable adhesive material located on the outside surface of the tubular body. The photodegradable adhesive is decomposed by energy in the first wavelength range, and the crosslinkable adhesive material is crosslinked by energy emitted by the fluorescent material.

According to yet another aspect of the invention, there is provided apparatus for placing a stent in a selected region of blood vessel. The apparatus comprises a flexible, elongated tube having an inflatable balloon at or near its distal end and a tubular body formed by rolling a sheet of biologically-compatible material so that portions of the sheet overlap. The tubular body, which has a crosslinkable adhesive material between overlapping portions of the sheet, is releaseably adhered to the outside surface of the balloon. The apparatus further comprises means for inflating the balloon to thereby urge the tubular body into contact with an inside surface of the blood vessel and means for applying energy to the tubular body at the selected region of the blood vessel with the balloon inflated so as to crosslink the adhesive material and cause overlapping portions of the sheet to adhere together to thereby form a stent.

According to a further aspect of the invention, there is provided an endovascular stent for placement in a selected region of a blood vessel. The stent comprises a generally tubular body formed by rolling a flexible sheet of biologically-compatible material so that portions of the sheet overlap. The tubular body has a crosslinkable adhesive material between overlapping portions of the sheet. The sheet can have a continuous surface or can be patterned with openings of various sizes and shapes.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
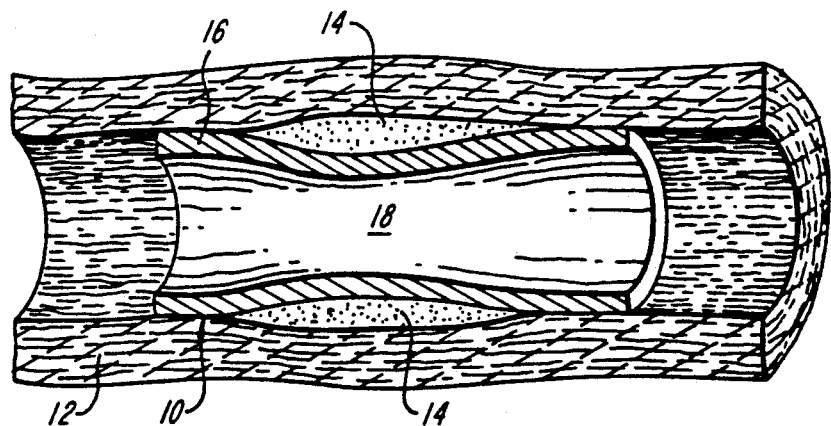
FIG. 1 is an enlarged, cross-sectional view of an artery having a collagen-based stent positioned therein.
Figure 6:
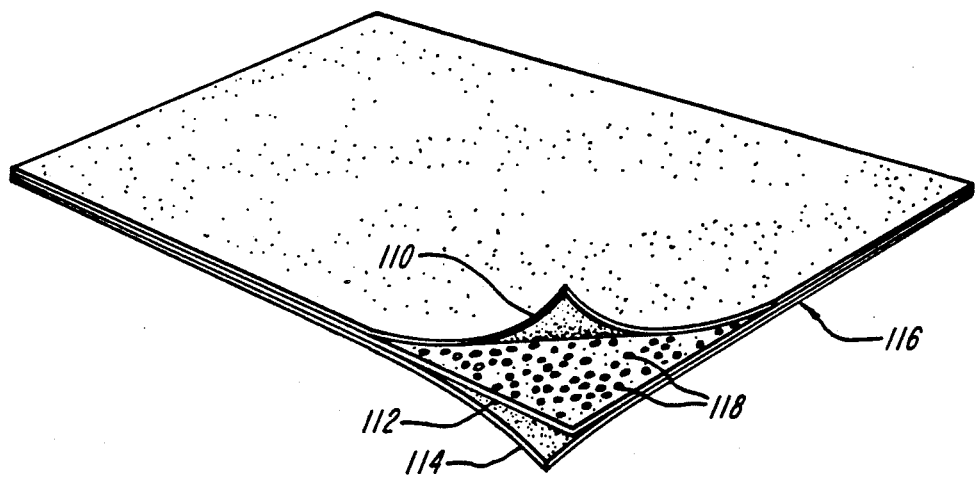
FIG. 6 is a perspective view of a sheet used for formation of an endovascular stent in accordance with another embodiment of the invention, with the adhesive layers rolled back for illustration.

In accordance with one aspect of the present invention, there is provided a formed-in-place endovascular stent for use in a blood vessel, typically an artery. The stent is composed at least in part of collagen to ensure compatibility with the blood vessel. As shown in FIG. 1, an endovascular stent 10 is positioned in an artery 12 at a selected location that may have plaque deposits 14. Typically, balloon angioplasty has been utilized to provide a widened passage through plaque deposits 14.

A collagen-based material for stent 10 is delivered to the selected location in artery 12 in the form of a liquid or a pliable solid. The liquid or pliable solid collagen-based material is uncured or partially cured until it is positioned at the selected location. The collagen-based material is formed at the selected location into the desired stent configuration. Typically, the stent 10 has a generally tubular configuration including a wall 16 which defines a lumen 18. The stent 10 may have an irregular shape to conform to the interior of artery 12. After the collagen-based material has been formed into the desired configuration in artery 12, energy, typically laser energy or thermal energy, is applied thereto, causing the collagen-based material to be crosslinked. Crosslinking of the collagen-based material causes it to become more rigid and to retain its shape, and to adhere to the wall of the artery. Techniques for delivery, formation and curing of stent 10 are described in detail hereinafter.

Figure 2:
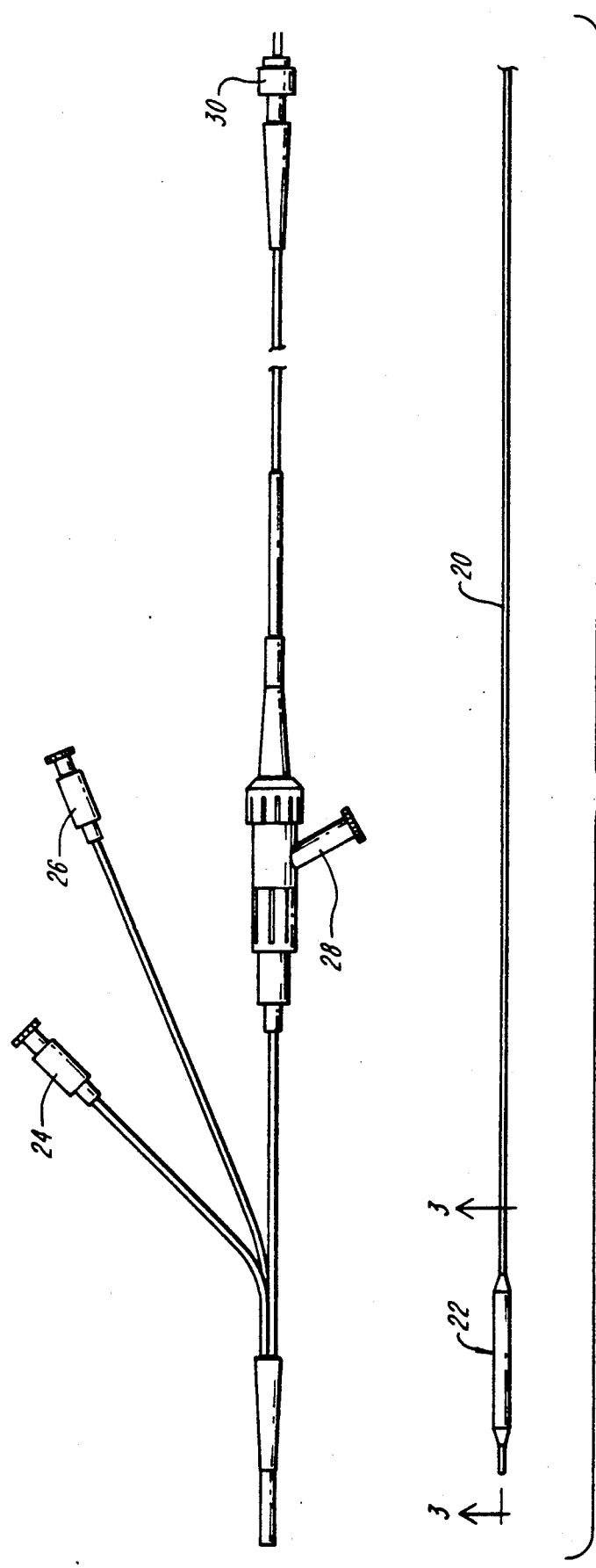
FIG. 2 is a an illustration of a laser balloon catheter suitable for delivery of a collagen-based stent.

The collagen-based material is advantageously delivered to the selected region of the artery with a laser balloon catheter as shown in FIG. 2. An elongated, flexible tube 20 has a laser balloon assembly 22 at its distal end and connectors 24, 26, 28 and 30 at its proximal end. The laser balloon assembly 22 includes an optical fiber tip assembly 34 (FIG. 3), for emitting laser radiation, a distal extension 36 of tube 20 for a guidewire (not shown) and for carrying a fluid to the treatment region, and a balloon 40 which is inflated and deflated from the proximal end of the flexible tube 20. An optical fiber extends from connector 30 through a lumen in the flexible tube 20 and terminates in optical fiber tip assembly 34.

The optical fiber tip assembly 34 is a diffusing tip which directs laser energy outwardly through balloon 40 in a generally uniform cylindrical radiation pattern. The balloon 40 is preferably fabricated of polyethylene terephthalate (PET). In one embodiment, the optical fiber tip assembly 34 includes a tapered optical fiber that has a spiral shape around distal extension 36 to prevent shadowing. Further details regarding the construction of the laser balloon catheter ar provided in pending application Ser. No. 106,609, filed Oct. 8, 1987, which is hereby incorporated by reference.

A collagen-based material 46 is adhered to the outer surface of balloon 40. The collagen-based material 46 is pliable and resilient so that the balloon 40 can be deflated for delivery to the selected region of the artery. When the balloon 40 is deflated, the collagen-based material 46 remains adhered to the balloon surface and collapses with the balloon. When the balloon 40 is inflated, the collagen-based material 46 is sufficiently resilient and pliable to unfold with the balloon. Preferably, the collagen-based material 46 is formed as a coating on balloon 40.

Figure 3:
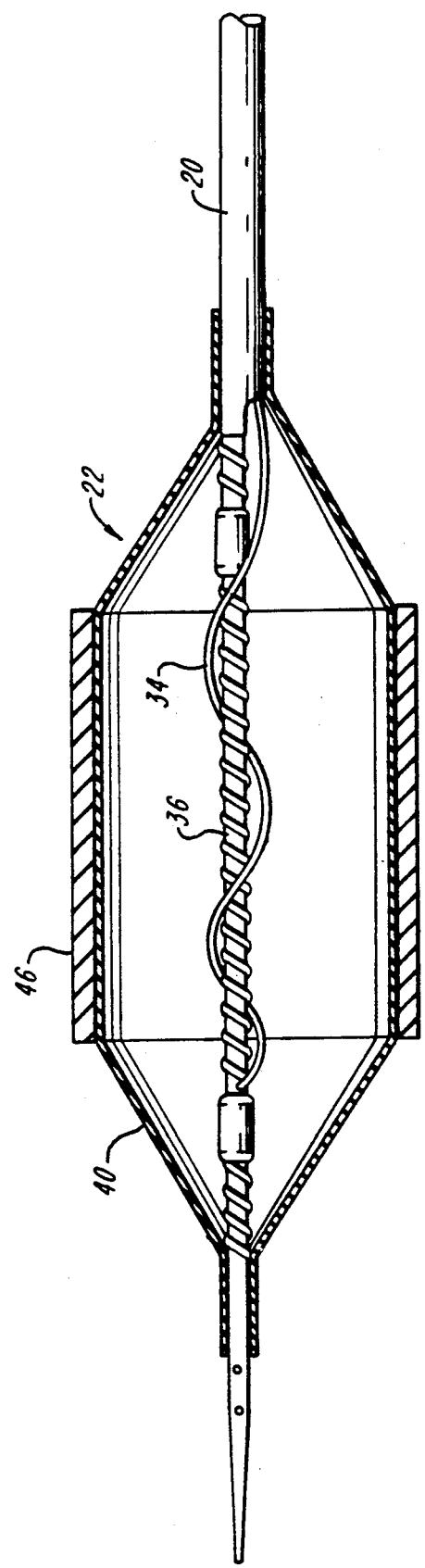
FIG. 3 is an enlarged, cross-sectional view of the distal end of the laser balloon catheter taken along the lines 3—3 of FIG. 2 and illustrating a technique for delivery of a collagen-based stent.

In use, the laser balloon catheter shown in FIGS. 2 and 3 is advanced through an artery to a stenosed region that has previously been treated by balloon angioplasty. The balloon 40 carrying collagen-based material 46 is positioned in the stenosed region. The balloon 40 is inflated so that the collagen-based material 46 is brought into contact with the inner surface of artery 12. After balloon 40 is inflated, laser energy from an external source is supplied through connector 30 and the optical fiber in tube 20 to tip assembly 34. The laser energy is diffused outwardly in a generally uniform cylindrical pattern causing collagen-based material 46 to be crosslinked. When the collagen based material is crosslinked, it becomes more rigid and forms a stent in the artery, as shown in FIG. 1. The laser energy is then turned off, and the stent is allowed to cool. After cooling, the balloon 40 is deflated. Since the stent 10 is now more rigid, it peels off the balloon and remains in place on the wall of artery 12 rather than collapsing with balloon 40. The laser balloon catheter is then withdrawn leaving stent 10 to maintain a passage and prevent flaps of plaque 14 from blocking the artery 12. Eventually, the stent 10 is absorbed into the tissue of the artery 12 so that a widened passage is maintained without the requirement for a metallic stent.

Figure 4:
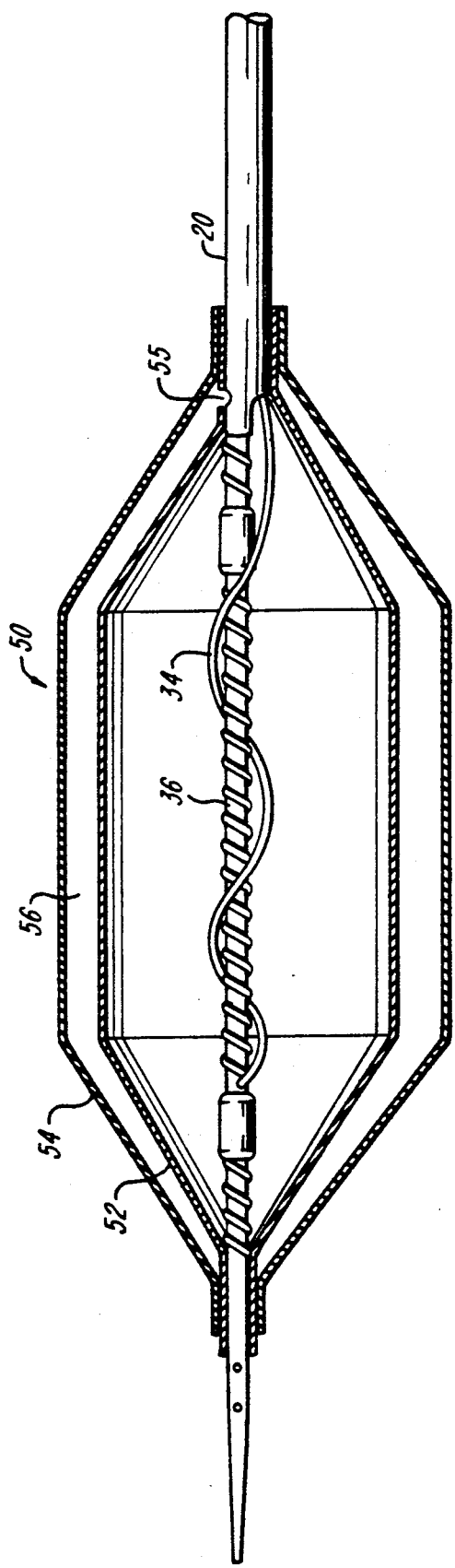
FIG. 4 is an enlarged, cross-sectional view of the distal end of the laser balloon catheter in accordance with another technique for delivery of a collagen-based stent.
Figure 5:
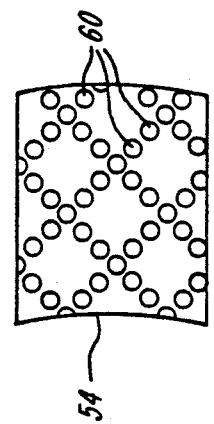
FIG. 5 is a fragmentary view of the outer balloon of FIG. 4 illustrating a pattern of openings in the balloon.

An alternative laser balloon catheter for delivery of a formed-in-place endovascular stent is shown in FIGS. 4 and 5. The device is a laser balloon catheter having a laser balloon assembly 50 as shown in FIG. 4. The laser balloon assembly 50 includes optical fiber tip assembly 34 and central shaft 36 at the distal end of flexible tube 20. An inner balloon 52 is sealed at one end to tube 20 and at the other end to central shaft 36. Balloon 52 can be inflated and deflated from the proximal end of tube 20. An outer balloon 54 surrounds inner balloon 52 and is sealed to flexible tube 20 and to central shaft 36 in a manner similar to inner balloon 52. A port 55 interconnects a lumen (not shown) in flexible tube 20 and a space 56 between balloons 52 and 54. Outer balloon 54 includes a multiplicity of pores or openings 60 (FIG. 5). Preferably, the openings 60 have a diameter of about 0.005-inch or less, depending on the viscosity of the collagen-based material.

The space 56 between inner balloon 52 and outer balloon 54 is filled with a liquid collagen-based material. The collagen-based material has sufficient viscosity to remain in the space 56 when inner balloon 52 is deflated. When inner balloon 52 is inflated, the collagen-based material is forced through the openings 60 in outer balloon 54 to form a layer of collagen-based material surrounding outer balloon 54. Since inner balloon 52 is inflated, the layer of collagen-based material is pushed outwardly into contact with the inside surface of the artery. Laser energy is then supplied through the optical fiber in flexible tube 20 to tip assembly 34. The laser energy is directed outwardly by tip assembly 34 through balloons 52 and 54, causing the layer of collagen-based material to be crosslinked. When the collagen-based material is crosslinked, it becomes more rigid and forms a stent in the selected region of the artery. The balloons 52 and 54 are then deflated, and the laser balloon catheter is withdrawn from the artery.

In one embodiment, the liquid collagen-based material is injected through port 55 into the space 56 between balloons 52 and 54 before the laser balloon assembly 50 is advanced t the stenosed region of the artery. In a second embodiment, the liquid collagen based material is injected through port 55 into the space 56 through on of the lumens in flexible tube 20 after the laser balloon assembly 50 has been positioned in the stenosed region of the artery.

The openings 60 in outer balloon 54 can be uniformly distributed over its surface with a spacing that is sufficiently close to permit the liquid collagen-based material to flow together after it passes through the openings. In this case, the collagen-based material forms a continuous layer on the wall of the artery. For an imperforate tubular stent, the openings 60 should have a uniform spacing of 5 to 10 times the diameter of openings 60. In another embodiment illustrated in FIG. 5, openings 60 in outer balloon 54 are patterned to form a mesh, grid or other desired pattern. When the liquid collagen-based material flows through openings 60, it forms a pattern that is determined by the pattern of openings 60. After crosslinking by laser radiation, the stent retains the pattern defined by openings 60. Thus, the stent may have a mesh or grid configuration which allows unobstructed blood flow to side branch arteries that are located at the site of the stent. For a mesh or grid configuration, the openings 60 should have a spacing of about 5 times the diameter of openings 60 along the lines of mesh and a spacing between lines of about 20 times the diameter of openings 60.

Types I-V collagens can be utilized for the formed-in-place endovascular stent described herein, since these collagens can be crosslinked. Type III collagens derived from the human cardiovascular system are preferred. Also, a number of Type I collagens can be utilized. A collagen derived from chicken ligaments and rat tail (99% pure) has been used in vitro. An example of preparation of a collagen stent is described below.

1. Type I bovine corium collagen available from Collagen Corporation, Palo Alto, Cal., is slowly dissolved in a 1% solution of glutaraldehyde (Grade 1-Sigma Corporation, St. Louis, Mo.), causing some crosslinking to occur in the collagen.

2. The solution is gently heated for 10-20 hours to remove non-biocompatible materials.

3. The solution is centrifuged for about 2 minutes at 7500 rpm to concentrate the collagen.

4. After the supernatant has been discarded, the sediment is introduced into the vascular system by a porous laser balloon catheter as shown in FIGS. 4 and 5 and described hereinabove. When the selected region of the artery is reached, laser energy at a wavelength of 350 nanometers or infrared radiation at 0.8 to 2.5 micrometers is applied through the balloon wall to complete the crosslinking process.

5. The stent thus formed remains in place from 20-90 days and is gradually absorbed by the body.

The collagen can be dissolved in any aldehyde containing solution since crosslinking occurs between amino groups. The amount of crosslinking can be controlled by varying the concentration of the aldehyde, the duration of exposure of the collagen to the aldehyde, or adjusting the number of available amino groups. Crosslinking is caused by the formation of covalent bonds and may be either intramolecular or intermolecular, depending on the type of collagen. Crosslinking increases the rigidity and the mechanical strength of the collagen, as described in *Science*, Vol. 232, June 13, 1986, pp. 1421-1422.

Light energy at various wavelengths can be utilized to effect crosslinking at the selected region of the artery. While ultraviolet radiation is preferable, visible and infrared radiation can also be utilized, depending on the collagen selected. In addition, thermal energy from any suitable source, such as a resistive heating element located within the inflatable balloon, can be utilized to effect crosslinking. External radio frequency energy or beta rays can also be used to effect crosslinking.

The invention has been described thus far in connection with formation of an endovascular stent utilized in blood vessels. The techniques described herein can also be utilized for treatment of wounds on the skin. A layer of collagen-based material with or without a support layer, such as PET, is positioned over the wound. The collagen-based material is in an uncured or partially cured state. Laser radiation is then applied to the collagen-based material causing crosslinking thereof and formation of a semi-rigid protective layer.

According to another aspect of the invention, an endovascular stent is formed by rolling a sheet of biologically-compatible material into a tubular configuration, as illustrated in FIGS. 6-9. A layer or coating of crosslinkable adhesive material 110 is applied to one side of a sheet 112 of biologically-compatible material. The adhesive material 110 is preferably a collagen-based material that can be crosslinked with ultraviolet, visible or infrared radiation to form a biologically-compatible adhesive. The sheet 112 is preferably a transparent, flexible, biologically-compatible polymer. As described in more detail hereinafter, the sheet 112 can have a continuous surface or can be patterned with openings of various sizes and shapes. The sheet 112 is preferably provided with a plurality of openings 118 so that blood flow to side branch blood vessels located at the stenosed region is not blocked by the stent. The sheet 112 can be porous to promote growth of endothelial cells. An optional layer or coating of photodegradable adhesive 114 can be applied to the sheet 112 on the side opposite adhesive material 110. The adhesive 114 is a material which degrades or decomposes and loses its adhesive properties upon the application of energy, typically ultraviolet, visible or infrared radiation. Further details regarding the adhesive material 110, the sheet 112 and the photodegradable adhesive 114 are provided hereinafter.

Figure 7:
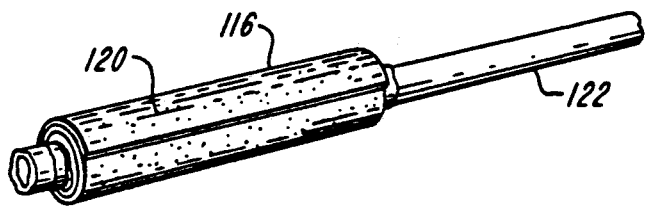
FIG. 7 is a perspective view of an inflatable balloon located at the distal end of a catheter and having the sheet of FIG. 6 rolled thereon to form an endovascular stent.

The sheet 112, adhesive material 110 and optional photodegradable adhesive 114 constitute a composite sheet 116 which is rolled to form a generally tubular configuration in which portions of the composite sheet 116 overlap. Typically, the composite sheet 116 is rolled to form one and one-half or more turns, with the adhesive material 110 located on the outside. Thus, the adhesive material 110 is present between overlapping portions of sheet 116 and typically covers the outside surface of the tubular configuration. The sheet 116 is preferably rolled around the outside surface of an inflatable balloon 120 located at the distal end of a catheter 122, as shown in FIG. 7. The balloon 120 and the catheter 122 can be fabricated in the same manner as the laser balloon catheter shown in FIGS. 2 and 3 and described hereinabove. The composite sheet 116 is rolled onto the deflated balloon 120 in a relatively small diameter configuration having two or more turns. The rolled composite sheet 116 in its tubular configuration constitutes an endovascular stent ready for delivery to a blood vessel.

Figure 8:
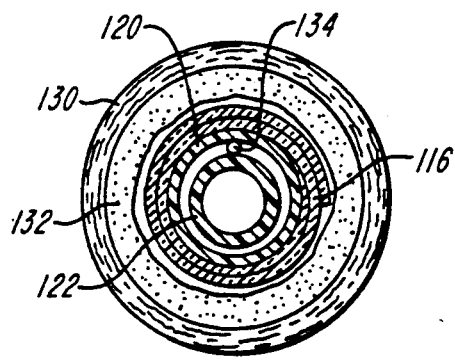
FIG. 8 is a cross-sectional view of the balloon and rolled sheet of FIG. 7 positioned in a stenosed artery, with the balloon deflated.
Figure 9:
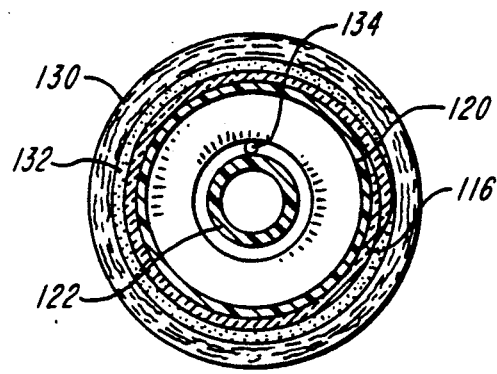
FIG. 9 is a cross-sectional view of the balloon and rolled sheet of FIG. 7 positioned in a stenosed artery, with the balloon inflated.

The catheter 122 and balloon 120 carrying the rolled sheet 116 are advanced to a stenosed region of an artery, as shown in cross-section in FIGS. 8 and 9. Artery 130 is partially blocked by plaque deposit 132. The stent described herein is typically used after treatment of the stenosed region with a conventional balloon catheter. The balloon 120 is positioned in the stenosed region and is inflated. Inflation of the balloon causes the rolled sheet 116 to partially unroll by sliding of the overlapping layers, and to assume a larger diameter. The balloon 120 is inflated sufficiently to bring the rolled sheet 116 into contact with the inside surface of the artery 130 or plaque deposit 132 such that the crosslinkable adhesive material is sandwiched between sheet 112 and the inside surface of the artery as shown in FIG. 9. The overlap of the rolled sheet 116 must be sufficient to insure at least some overlap after the balloon 120 is inflated.

After the balloon 120 is inflated, laser energy from an external source is supplied through an optical fiber in the catheter to optical fiber tip assembly 134. The wavelength of the laser energy is in a range selected to crosslink the adhesive material 110. The laser energy is diffused outwardly in a generally uniform, cylindrical pattern, as described in connection with FIGS. 2 and 3, causing the adhesive material 110 to be crosslinked. When the adhesive material 110 is crosslinked, it attaches overlapping portions of sheet 112 to each other, thereby forming a stent in the stenosed region. The attachment of overlapping portions of sheet 112 by crosslinking of adhesive material 110 locks the rolled layers together in a fixed configuration. The laser energy is then turned off, and the stent is allowed to cool. After cooling, the balloon 120 is deflated and the catheter is withdrawn, leaving the stent in place.

Optionally, the adhesive material 110, which covers the outside surface of the tubular configuration of composite sheet 116, is used to attach the sheet 112 to the artery. The attachment of the stent to the artery by crosslinking of adhesive material 110 with laser energy insures that the stent will not move in the artery.

As indicated previously, a layer or coating of photodegradable adhesive 114 can be utilized on the inside surface of rolled sheet 112. The photodegradable adhesive 114 is used to attach the tubular sheet 112 to inflatable balloon 120 until the balloon 120 has been advanced to the stenosed region. When the balloon 12 carrying the rolled sheet 116 has been advanced to the stenosed region of the artery, laser energy in a wavelength range selected to degrade and decompose adhesive 114 is transmitted through the optical fiber to the tip assembly 134. The rolled sheet 116 is released from the balloon 120 for placement by inflating the balloon 120 and applying laser energy of a wavelength selected to crosslink adhesive material 110, as described above. The photodegradable adhesive 114 insures that the rolled sheet 116 remains affixed to the balloon 120 during delivery through the artery to the stenosed region.

The sheet 112 can be any material that is suitable for implantation in the human body and can be formed into a flexible sheet that is suitable for rolling onto an inflatable balloon. Biologically-compatible polymers can be utilized. An example of such a material is a sheet of polylactic acid having a thickness in the range of about 10 to 100 micrometers. The sheet of biologically compatible material can remain in the blood vessel or can be a material that is gradually absorbed into the human body. The crosslinkable adhesive material 110 is preferably a collagen-based material that can be crosslinked with light energy. One example of such material is collagen with riboflavin, which can be crosslinked with visible or near-ultraviolet radiation. Adhesive materials that are crosslinkable with thermal energy or microwave energy can also be utilized. The primary requirement is that the adhesive material 110 be biologically-compatible and be crosslinkable with energy that can be transmitted through the catheter to the stenosed region. An example of the photodegradable adhesive 114 for use on the inside surface of the sheet 112 is a polyamide. Polyamides are typically decomposed by ultraviolet radiation. Another example of the photodegradable adhesive is nitrocellulose.

Figure 10:
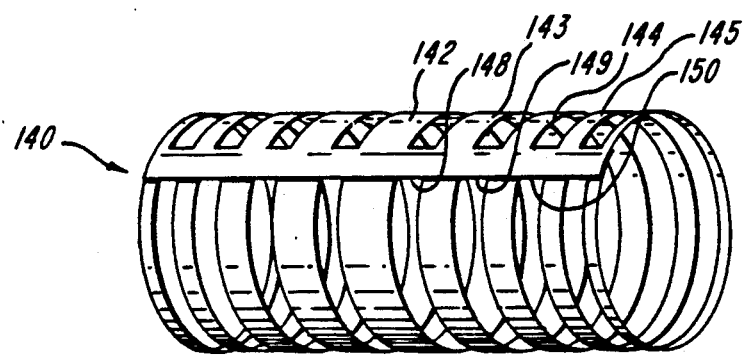
FIG. 10 is an illustration of a stent formed as a plurality of interconnected rings in accordance with a further embodiment of the invention.

The sheet 112 has been described thus far as having a continuous surface or a surface provided with holes 118 to permit blood flow to side branches. Another embodiment of a stent formed from a rolled sheet of biologically-compatible material is shown in FIG. 10. A stent 140 is formed as a plurality of rings 142, 143, 144, 145, etc. which are coaxial, have approximately the same diameters and are interconnected by axial segments 148, 149, 150, etc.

The open structure of the stent 140 is more flexible than a closed or continuous stent and also permits blood flow to side branches in the region of the stent. The rings 142, 143, 144, 145, etc. can have different widths to provide variable flexibility along the length of the stent. Wide rings provide relatively low flexibility, while narrow rings provide relatively high flexibility. The stent 140 as shown in FIG. 10 is formed by rolling a patterned sheet of biologically-compatible material into a generally tubular configuration. The patterned sheet comprises multiple strips corresponding to rings 142, 143, 144, 145, etc. The strips are defined by slots between them and are interconnected by segments 148, 149, 150, etc. A layer or coating of crosslinkable adhesive material is applied to one side of the patterned sheet, and an optional layer or coating of photodegradable adhesive is applied to the opposite side of the patterned sheet. The stent 140 is delivered to a selected region of a blood vessel in the same manner described hereinabove in connection with FIGS. 6-9. Thus, it will be understood that as used herein, the term "sheet" means either a continuous sheet or a patterned sheet having holes, slots or openings of any size or shape. The sheet is rolled into a generally tubular configuration to form a stent.

According to a further feature of the invention, a fluorescent material is incorporated into the photodegradable adhesive 114. The fluorescent material absorbs radiation in a first wavelength range and emits radiation in a second wavelength range. The fluorescent material is selected such that the absorbed radiation in the first wavelength range is suitable for decomposing the photodegradable adhesive 114. The fluorescent material is also selected such that the emitted radiation in the second wavelength range crosslinks the adhesive material 110 on the outer surface of the rolled sheet 112. Thus, laser radiation in a single wavelength range is used both to decompose adhesive 114 and to stimulate the fluorescent material for crosslinking of the adhesive material 110. An example of a suitable fluorescent material is a laser dye such as coumarin dye which emits radiation in the blue/green range when stimulated by ultraviolet radiation. The laser dye or other fluorescent material is mixed with the photodegradable adhesive 114 prior to application to the sheet 112.

The composite sheet 116 has been described hereinabove as being expanded by inflation of balloon 20. The sheet 112 can be fabricated with sufficient resilience to expand to a larger diameter of its own accord when released from the balloon 120 by irradiation of photodegradable adhesive 114.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for treating a selected region of a blood vessel, comprising the steps of:

applying a crosslinkable adhesive material to one side of a flexible sheet of biologically-compatible material;

rolling the sheet of biologically-compatible material so that portions of the sheet overlap to form a generally tubular body, said tubular body having said crosslinkable adhesive material between overlapping portions of the sheet;

delivering the tubular body to the selected region of the blood vessel; and applying energy to the tubular body at the selected region of the blood vessel so as to crosslink the adhesive material and cause overlapping portions of the sheet to adhere together to thereby form a stent in the blood vessel.

2. A method as defined in claim 1 wherein the step of applying a crosslinkable adhesive material includes applying a crosslinkable collagen-based material.

3. A method as defined in claim 1 wherein the step of rolling the sheet of biologically-compatible material includes rolling the sheet onto an outer surface of an inflatable balloon located at or near the distal end of a catheter.

4. A method as defined in claim 3 wherein the step of delivering the tubular body includes advancing the catheter through the blood vessel until the balloon is positioned at the selected region.

5. A method as defined in claim 4 further including the step of inflating the balloon to thereby increase the diameter of the tubular body and urge the tubular body into contact with an inside surface of the blood vessel.

6. A method as defined in claim 1 wherein the step of applying energy includes applying light energy to the tubular body.

7. A method as defined in claim 1 wherein the step of applying energy includes applying diffused laser energy to the tubular body.

8. A method as defined in claim 3 further including the step of applying a photodegradable adhesive to the other side of the sheet of biologically-compatible material prior to the step of rolling the sheet onto an inflatable balloon so that said tubular body is adhered to said inflatable balloon by said photodegradable adhesive.

9. A method as defined in claim 8 wherein the step of applying energy to the tubular body includes applying energy i a first wavelength range selected to degrade said photodegradable adhesive and release said tubular body from said inflatable balloon in the selected region of the blood vessel.

10. A method as defined in claim 9 wherein said photodegradable adhesive includes a fluorescent material that is stimulated by energy in said first wavelength range to emit energy in a second wavelength range required for crosslinking of said crosslinkable adhesive material so that said photodegradable adhesive is degraded by energy in said first wavelength range and said crosslinkable adhesive material is crosslinked by energy emitted by said fluorescent material.

11. A method as define din claim 2 wherein said collagen-based material comprises a collagen containing riboflavin and the step of applying energy includes applying energy int he visible or near-ultraviolet wavelength range.

12. A method as defined in claim 8 wherein said photodegradable adhesive comprises a polyamide.

13. A method as defined in claim 8 wherein said photodegradable adhesive comprises nitrocellulose.

14. A method as defined in claim 10 wherein said fluorescent material comprises a laser dye.

15. A method as defined in claim 1 wherein said sheet has a continuous surface.

16. A method as defined in claim 1 wherein said sheet is patterned with a plurality of openings.

17. A method as defined in claim 1 wherein said crosslinkable adhesive material is applied to an outside surface of said tubular body and wherein the step of applying energy to the tubular body causes the tubular body to be attached to the blood vessel.

18. A combination of a stent and an apparatus for placing a stent in a selected region of a blood vessel, comprising:

a flexible, elongated tube having an inflatable balloon at or near its distal end;

a generally tubular body comprising a sheet of biologically-compatible material rolled onto said balloon so that portions of the sheet overlap, said tubular body having a crosslinkable adhesive material between overlapping portions of the sheet, said tubular body being releaseably adhered to the outside surface of said balloon;

means for inflating said balloon to thereby urge said tubular body into contact with an inside surface of said blood vessel; and means for applying energy to the tubular body at the selected region of the blood vessel with said balloon inflated so as to crosslink the crosslinkable adhesive material and cause overlapping portions of the sheet to adhere together to thereby form a stent.

19. Apparatus as defined in claim 18 wherein said biologically-compatible material comprises polylactic acid.

20. Apparatus as defined in claim 18 wherein said crosslinkable adhesive material comprises a collagen-based material.

21. Apparatus as defined in claim 20 wherein said collagen-based material comprises a collagen containing riboflavin.

22. Apparatus as defined in claim 18 wherein said means for applying energy includes mean for applying light energy.

23. Apparatus as defined in claim 18 wherein said means for applying energy includes means for applying diffused laser energy.

24. Apparatus as defined in claim 18 wherein said tubular body is releaseably adhered to said balloon with a photodegradable adhesive.

25. Apparatus as defined in claim 24 wherein said photodegradable adhesive comprises a polyamide.

26. Apparatus as defined in claim 24 wherein said photodegradable adhesive comprises nitrocellulose.

27. Apparatus as defined in claim 24 wherein said photodegradable adhesive includes a fluorescent material that is stimulated by energy in a first wavelength range selected to degrade said photodegradable adhesive and release said stent, said fluorescent material emitting energy in a second wavelength range required for crosslinking of said crosslinkable adhesive material when stimulated by energy in said first wavelength range.

28. Apparatus as defined in claim 18 wherein said tubular body has said crosslinkable adhesive material on an outside surface thereof and said means for applying energy to the tubular body causes the tubular body to be attached to the blood vessel.

29. Apparatus as defined in claim 18 wherein said sheet has a continuous surface.

30. Apparatus as defined in claim 18 wherein said sheet is patterned with a plurality of openings.

31. An endovascular stent in a selected region of a blood vessel comprising a tubular body formed as a rolled sheet of biologically-compatible material wherein portions of the sheet overlap, said tubular body having a crosslinked adhesive material between overlapping portions of the sheet.

32. An endovascular stent as defined in claim 31 wherein said biologically-compatible material comprises a polymer.

33. An endovascular stent as defined in claim 31 wherein said biologically compatible material comprises polylactic acid.

34. An endovascular stent as defined in claim 31 wherein said crosslinked adhesive material comprises a collagen-based material.

35. An endovascular stent as defined in claim 34 wherein said collagen-based material comprises a collagen containing riboflavin.

36. An endovascular stent as defined in claim 31 further including a photodegradable adhesive on an inside surface of said tubular body.

37. An endovascular stent as defined in claim 36 wherein said photodegradable material comprises a polyamide.

38. An endovascular stent as defined in claim 36 wherein said photodegradable material comprises nitrocellulose.

39. An endovascular stent as defined in claim 36 wherein said photodegradable adhesive includes a fluorescent material that is stimulated by energy in a first wavelength range selected to degrade said photodegradable adhesive and release said stent, said fluorescent material emitting energy in a second wavelength range required for crosslinking of said crosslinkable adhesive material when stimulated by energy in said first wavelength range.

40. An endovascular stent as defined in claim 31 wherein said tubular body has said crosslinked adhesive material on an outside surface thereof.

41. An endovascular stent as defined in claim 31 wherein said sheet has a continuous surface.

42. An endovascular stent as defined in claim 31 wherein said sheet is patterned with a plurality of openings.

43. An endovascular stent as defined in claim 42 wherein said tubular configuration comprises a plurality of interconnected rings.

44. An endovascular stent as defined in claim 43 wherein interconnected rings have different widths to provide variable flexibility along the length of the stent.

* * * * *